(12) United States Patent
Wilson et al.

(10) Patent No.: US 8,736,453 B2
(45) Date of Patent: May 27, 2014

(54) PREEMPTIVE NOTIFICATION OF PATIENT FALL RISK CONDITION

(75) Inventors: Jason Wilson, Toronto (CA); Richard Mayoras, Kalamazoo, MI (US)

(73) Assignee: Globestar Systems, Inc., Toronto (CA)

( * ) Notice: Subject to any disclaimer, the term of this patent is extended or adjusted under 35 U.S.C. 154(b) by 153 days.

(21) Appl. No.: 13/551,540

(22) Filed: Jul. 17, 2012

(65) Prior Publication Data

US 2014/0022079 A1   Jan. 23, 2014

(51) Int. Cl.
*G08B 23/00* (2006.01)

(52) U.S. Cl.
USPC ...................................... 340/573.1

(58) Field of Classification Search
CPC .... A61B 5/1115; A61B 5/002; A61B 5/1117; G08B 21/02; G08B 21/043; G06F 19/3406; A47C 21/08
USPC ............ 340/573.1, 286.07, 539.12, 506, 517, 340/524, 13.24
See application file for complete search history.

(56) References Cited

U.S. PATENT DOCUMENTS

| | | | | |
|---|---|---|---|---|
| 7,746,218 | B2* | 6/2010 | Collins et al. | 340/286.07 |
| 7,852,208 | B2* | 12/2010 | Collins et al. | 340/539.12 |
| 2007/0010719 | A1* | 1/2007 | Huster et al. | 600/300 |

FOREIGN PATENT DOCUMENTS

EP   2392304 A1   7/2011

* cited by examiner

*Primary Examiner* — Phung Nguyen
(74) *Attorney, Agent, or Firm* — Robert Schuler

(57) ABSTRACT

One or more servers and hospital beds are connected to a healthcare network. At least one of the servers includes an event notification module that operates to receive patient EMR information and patient bed configuration information. The patient EMR information is comprised of a patient fall risk profile. At least one of the patient beds includes sensors that transmit messages which include information about the current bed configuration state to the event notification module. The event notification module uses information included in the patient fall risk profile and current bed configuration information to determine whether a patient is at risk of fall out of their bed, and if the patient is at risk, generates an alert message that is sent to a call station or hospital worker.

24 Claims, 8 Drawing Sheets

HOSPITAL HEALTHCARE SYSTEM 10

FIG. 3A

MINIMUM BED CONFIG. / FALL RISK TYPE

| RISK TYPE | MINIMUM BED CONFIGURATION |
|---|---|
| HIGH | THREE RAILS UP, BED LOW, BRAKE ON |
| MEDIUM | TWO RAILS UP, BRAKE ON |
| LOW | BRAKE ON |

FIG. 3B

PATIENT FALL RISK PROFILE

| PATIENT ID | FALL RISK TYPE |
|---|---|
| PATIENT 1 | HI |
| PATIENT 2 | MED |
| PATIENT n | LO |

FIG. 3C

PATIENT FALL RISK PROFILE

| PATIENT ID | FALL RISK CRITERIA | BED CONFIGURATION |
| --- | --- | --- |
| PATIENT 1 | CAN'T STAND UNASSISTED | ALL RAILS UP BED MED. HEIGHT |
| PATIENT 2 | NEED ASSISTENCE TO WALK | THREE RAILS UP |
| PATIENT n | CAN'T WALK | ALL RAILS UP, BED LOW HEIGHT |

FIG. 3D

CURRENT BED CONFIGURATION STATE

PATIENT ID/FALL RISK
BED ID
STATUS OF ALL BED PROPERTIES

PREEMPTIVE NOTIFICATION OF PATIENT FALL RISK CONDITION

BACKGROUND

1. Field of the Invention

The present disclosure relates generally to healthcare systems for capturing and maintaining patient healthcare records and employing information in the records to proactively alert hospital workers to a condition that places patient health at risk.

2. Background

A healthcare provider, such as a hospital, typically admits and treats some number of patients on a daily basis. Upon admission to the hospital, a healthcare worker can create a record that includes medical and/or personal information associated with each patient. Depending upon the size of the hospital, the healthcare provider can create and maintain a very large number of these medical records, and such records are typically created and then stored as an electronic medical record (EMR) in a healthcare system. Depending upon the size of the hospital, the healthcare system can operate in a single computational device, such as a personal computer or other device, or the healthcare system can be distributed in a plurality of computational devices that are connected to over a network (healthcare system network or simply the Network) to one or more servers which operate to, among other things, capture and store the electronic medical records. In addition to including patient medical information, an EMR can also include the identity and location (hospital room) of a hospital bed to which a patient is assigned. Hospital beds are available that include physical and physiological sensors which are connected over the Network to the Healthcare System. Information (telemetry) collected by the sensors can be processed at the bed by a controller or can be transmitted to the Hospital System for processing and storage in an EMR associated with the patient currently occupying the bed.

FIG. 1 is a diagram showing functionality included in a hospital healthcare system 10 that allows it to receive and store information from both healthcare workers and hospital beds. A server 11 is shown connected over one or more links to the healthcare system 10 network. The server 11 generally operates to capture and maintain a store 12 of patient EMRs, and it has a bed telemetry processing function 14 that operates to capture and process information received from hospital beds connected to the network. The sever 11 also has an event notification module 13 that can access information in the EMR store 12 and bed telemetry information to determine whether an alert message should be sent to a hospital worker or call point connected to the healthcare system 10. Alternatively, a database management system (DBMS) running on the healthcare system server 11 can operate to maintain the patient electronic medical records and maintain hospital bed configuration status information in a database 15 where the information can be accessed by the event notification module 13.

Healthcare organizations, such as a hospital or other care facility, have identified many patient health risks that are directly associated with care the patient receives while a resident in the facility. Some of these risks are associated with the physiological health of the patient, such as the risk of stroke or heart attack, or the risk of congestive heart failure for instance. Other types of risk can be associated with the physical well being of a patient, such as whether a patient is a fall risk. Typically upon admission to a healthcare organization, each patient can be evaluated to determine the degree to which they are at risk of falling. This evaluation process can include a physical examination to observe a patient's motor skills and balance, and/or it can include simply observing a patient or questioning the patient about their fall history. Regardless of the protocol employed to quantify the fall risk of a particular patient, a fall risk can be assigned to each patient and entered into a healthcare system, such as the healthcare system 10 described earlier, and stored in the patients EMR. A patients EMR can be easily accessed by a healthcare worker, such as a nurse, nurses aid or physician, in order to determine whether or not a patient is at risk of falling, and if so the level or degree to which the patient is at risk. Depending upon the patient's fall risk level, the patient's bed can be set up or configured by the healthcare worker in a manner that can prevent the patient from accidentally falling out of the bed, or at the bed can be set up so that the patient can more easily enter and exit the bed.

Hospital beds, such as the bed illustrated in FIG. 2, can be configured to include a number of different types of sensors, and the bed can be connected, over the network, to a healthcare system. Some bed sensors function to detect a patients weight in one or more positions on the surface of a bed, other bed sensors detect whether or not bed side rails are engaged in a full up position or not, some bed sensors operate to detect the angle at which one portion of a bed meets another portion of the bed, and still other bed sensors can detect physiological characteristics of a patient such as heart rate, respiratory rate, blood pressure to name only three characteristics. The sensors included in each bed can be connected to a central bed control mechanism which can operate to receive/capture information (telemetry) from each of the sensors, and can process the telemetry prior to transmission over a network link to a healthcare system or send the sensor telemetry to the healthcare system for processing. The healthcare system can then process the information received from the bed sensors to determine whether a healthcare worker should be notified of an event, such as a patient having exited their bed or a change in a patient's physiological measurement such as heart rate, blood pressure or respiratory rate as detected by bed sensors. Typically, a healthcare system can generate an alert in the event that a change to any one or more of a patient's physiological measurements is greater than a threshold amount, and the healthcare system is typically not capable of determining whether the physiological changes to the patient place the patient at risk of some adverse health event, such as a stroke.

BRIEF DESCRIPTION OF THE DRAWINGS

The present invention can be best understood by reading the specification with reference to the following Figures, in which:

FIG. 3A shows the format of and information included in a fall risk type.

FIG. 3B shows the format of a patient fall risk profile

FIG. 3C shows information included in a current bed configuration state.

FIG. 3D shows an example format of a bed configuration record.

DETAILED DESCRIPTION

Figure 1:
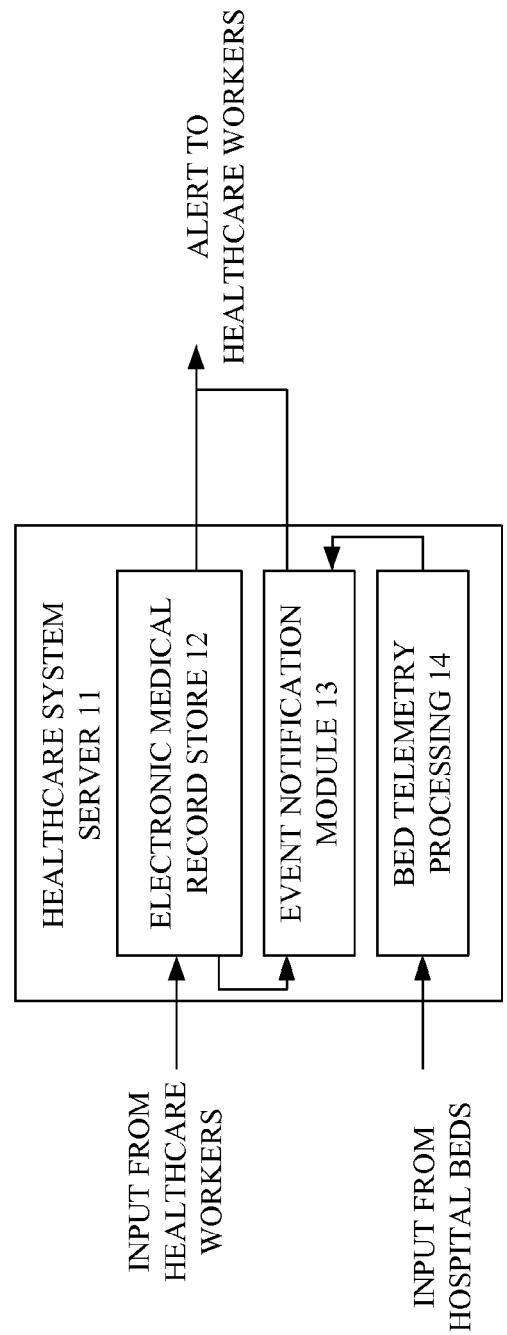
FIG. 1 is diagram of a Hospital Healthcare System 10.
Figure 2:
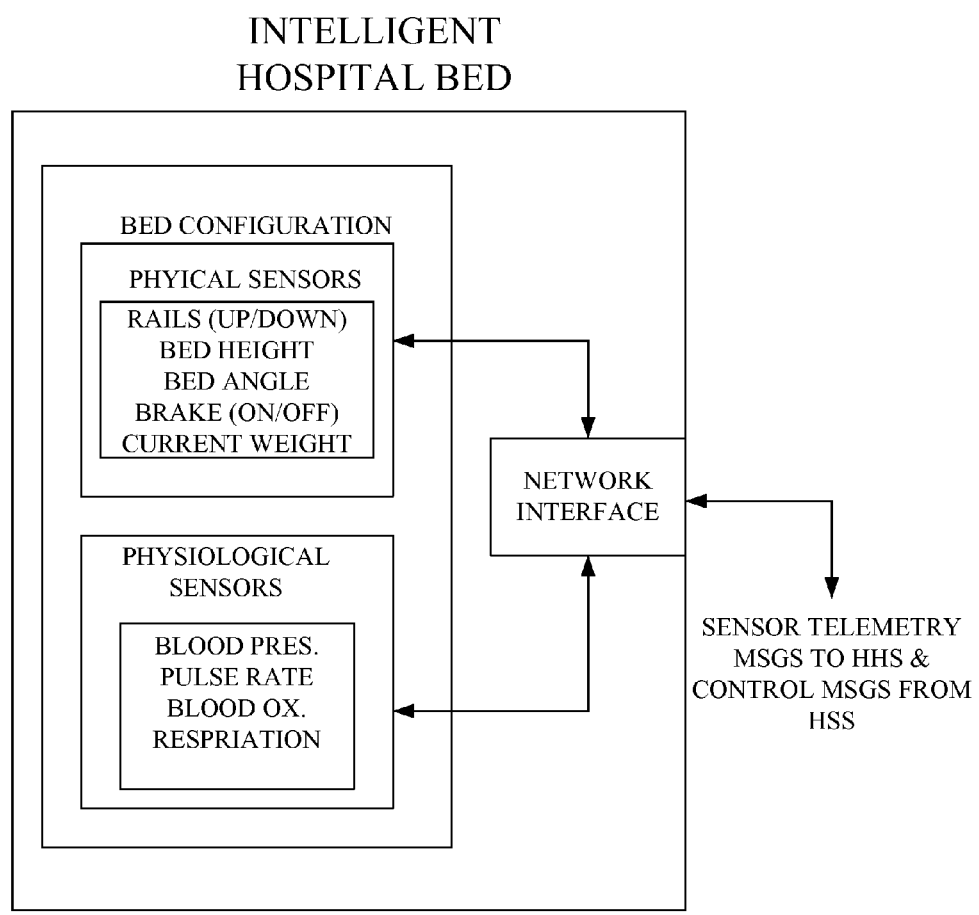
FIG. 2 is a diagram of an intelligent hospital bed.

The benefits to a patient in a healthcare system that can operate to proactively warn healthcare workers of an adverse patient condition are apparent. The ability to identify which patients may suffer possible, future adverse health events, such as a stroke or congestive heart failure, can either extend or save a patient's life. While physiological measures of a patient's health can be employed to proactively alert healthcare workers of an impending patient health crisis, healthcare systems do not currently operate to proactively alert healthcare workers to an elevated patient fall risk, such as a hospital bed configuration that could lead to a patient accidentally falling out of their hospital bed, or falling while attempting to enter their bed.

The short comings of the prior art healthcare systems are overcome in a healthcare system that proactively alerts healthcare workers to a bed configuration change that elevates a patients risk of falling out of their bed, or falling while attempting to enter their bed. With the knowledge that a patient is currently in their bed or not in their bed, knowing the patient's fall risk profile, knowing the minimum hospital bed configuration associated with the patients fall risk profile, and knowing the current bed configuration state, the healthcare system can generate an alert to one or more healthcare workers indicating that the patient's risk of falling is elevated above an acceptable level. More specifically, the healthcare system can include a patient fall risk processing function that operates to compare a current patient bed configuration to a minimum bed configuration corresponding to a patient's fall risk profile, and if the current bed configuration does not meet the minimum bed configuration (less than the minimum configuration), then an alert can be generated by the healthcare system for transmission to one or more healthcare workers. After receiving the alert, the healthcare worker can modify the current bed configuration to meet the minimum bed configuration and the healthcare system can either clear the previously transmitted alert and/or it can send another alert indicating that the bed configuration has been corrected. With the knowledge that the current configuration of a patient's hospital bed places them in an elevated risk of falling, accidental patient falls can be mitigated or prevented.

The formats of and information comprising an illustrative fall risk type, a patient fall risk profile and a current bed configuration are now described with reference to FIG. 3A-3D respectively. FIG. 3A identifies three generic fall risk types (high, medium, low), with each fall risk type corresponding to a particular minimum hospital bed configuration. In this case, the minimum bed configuration specified for a high fall risk type patient requires that three bed rails in the full up position, the bed height is adjusted to be low and a bed brake is on. These fall risk types can be defined and entered into a healthcare system by a healthcare organization based upon a corpus of patient fall risk information included in EMR's over some period of time.

FIG. 3B is illustrative of one or more patient fall risk profiles. All of these profiles can be stored in a patient EMR. A plurality of patients, patient 1 to patient n (with n being an integer value), are identified, and each of the patients identified is assigned a generic fall risk type. For example, patient 1 is assigned risk type high, and so forth to patient n which is assigned a fall risk type of low. Alternatively, a patient's risk profile does not include a generic fall risk type, but instead is comprised of one or more fall risk criteria. The fall risk criteria can be identified during an initial patient fall risk assessment and can include a description of a patients symptoms (physical and/or physiological) that can affect the patients mobility or ambulatory characteristics. Such a fall risk criteria description can include a description of assistance a patient needs in order to stand up, sit down and/or walk. The criteria description can indicate that a patient cannot stand without being assisted by a hospital worker, or that they can stand without assistance but they are not able to walk without the assistance of a cane/walker/hospital worker. The criteria description can indicate that due to blood pressure issues the patient becomes light headed when they attempt to stand or that the patient suffers from vertigo. In the event that a patients fall risk profile does not include a generic fall risk type, but rather includes one or more fall risk criteria, then a patient fall risk profile is formatted according to FIG. 3C.

FIG. 3C shows a plurality of patient fall risk profiles each of which include three fields. A first field includes patient identification information, a second field includes fall risk criteria information and a third field includes bed configuration information specifically tailored to each patients fall risk criteria. With respect to patient 1, the fall risk criteria field includes information indicating that the patient is not able to stand without assistance from a hospital worker, and the corresponding bed configuration profile is then specified to include how the bed should be configured to prevent the patient from accidentally falling out of the bed and bed configuration information that allows the patient to easily enter and exit their bed, which in this case is that all bed rails should be in the full up position and the bed should be set to a medium height above the floor.

FIG. 3D is an example format of a current bed configuration record that is comprised of at least the identity of a patients bed, the identify of a patient assigned to the bed and their fall risk assessment, and which includes the current status of the bed properties (current bed status) as determined by the healthcare system 10 from information/telemetry received from the bed sensors. Bed properties in the context of this description refers to, among other things, the number and types of bed rails included on a hospital bed, whether the bed has a height sensor, whether a bed can tilt, whether the bed includes weight sensors and the position of the weight sensors in the bed. In the preferred embodiment, the current bad property status can be, among other things, a determination that one or more rails are fully up or down, a determination as to the height of the bed above floor level and the tilt angle of the bed.

Figure 4:
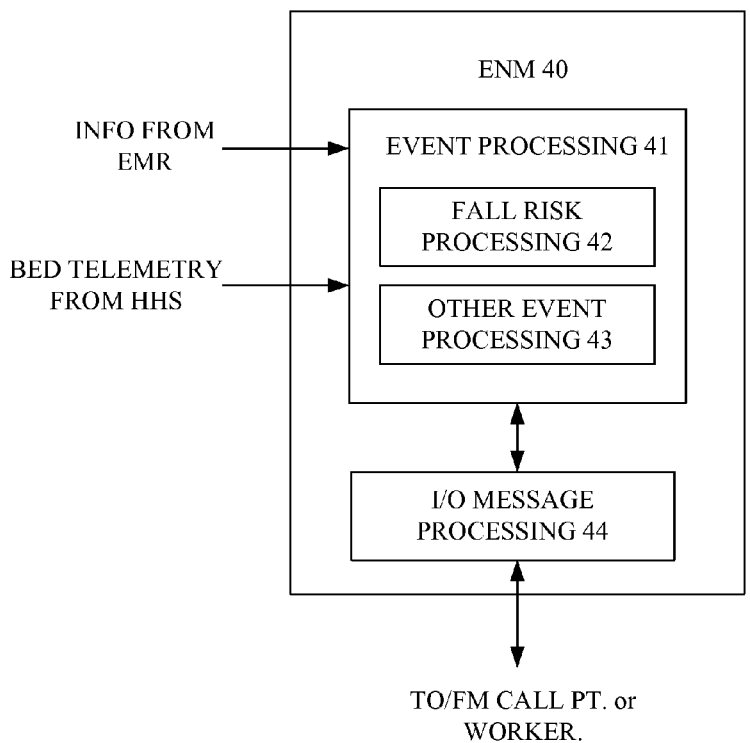
FIG. 4 is a functional block diagram of one embodiment of an event notification module.

FIG. 4 is illustrative of an event notification module (ENM) 40 that can be implemented in a server connected to a healthcare network, such as the healthcare network described with reference to FIG. 1. The ENM 40 operates on information comprising a patient EMR, information relating to a current bed status and a generic fall risk type to determine whether to generate and send an alarm to a hospital worker or call station indicating that a patient fall risk is greater than a selected threshold. The threshold can be set to a particular numerical value or it can be a minimum bed configuration similar to the minimum bed configuration described with reference to FIG. 3A. Alternatively, the ENM 40 does not employ the generic fall risk type to determine whether to generate an alert, but rather uses patient fall risk criteria. The ENM 40 is generally comprised of an event processing function 41, an input/output message (alarm) processing function 44 and may or may not have access to a database, such as the database 15 described earlier with reference to FIG. 1. The event processing function 41 can be comprised of a fall risk processing function or client 42 and other event processing clients as necessary for processing different classes of events. The fall risk processing client 42 can operate on, among other things, information in a patient's EMR and current bed configuration information to determine whether to send an alert to a call point or healthcare worker. In the event that an alert is generated by the event processing function 41, the information in the alert is sent to the input/output message processing function 44 which operates to determine which of one or more healthcare workers or call points should receive the alert. After receiving the alert, the healthcare worker can correct/modify the current bed configuration to at least meet the minimum hospital bed properties configuration necessary to mitigate the patient fall risk. Further, the healthcare system can detect that the bed configuration is modified/corrected by the healthcare worker to meet the minimum bed properties configuration and either cancel the earlier transmitted alert or send another alert indicating that the patient is no longer at risk of falling.

Figure 5:
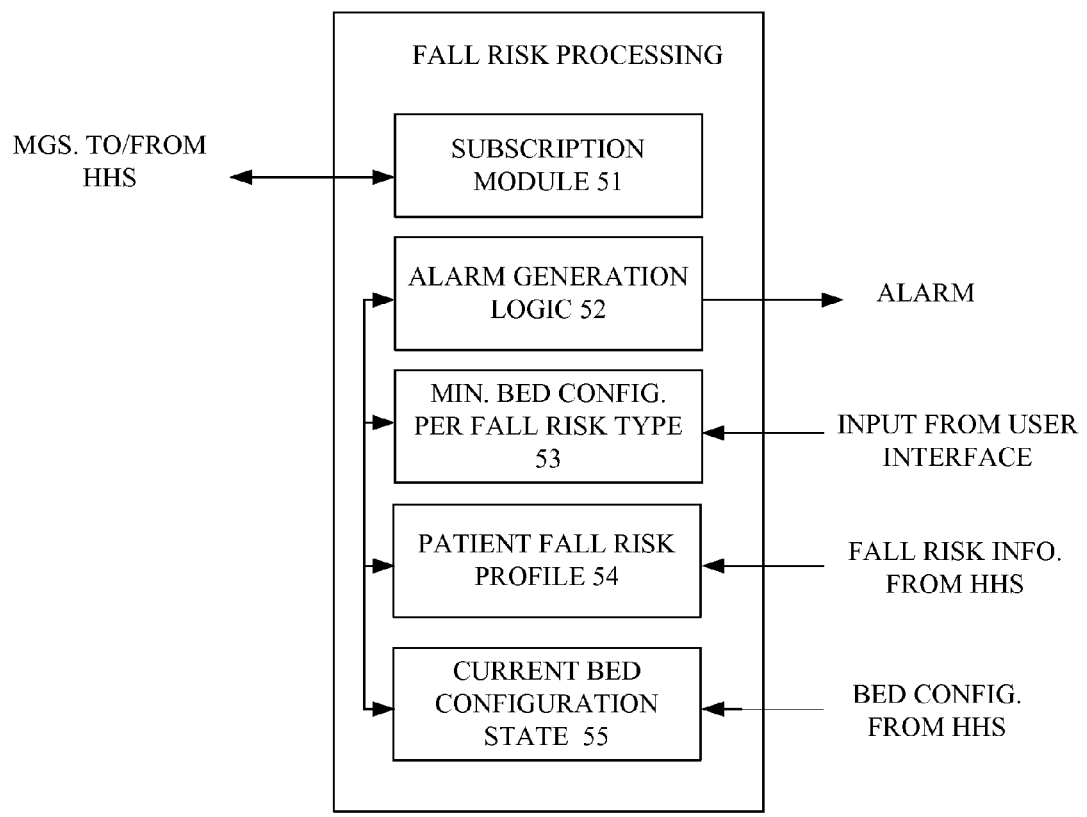
FIG. 5 is a functional block diagram of one embodiment of a fall risk processing client.

The fall risk processing function or client 42 is now described in greater detail with reference to FIG. 5. The client 42 is comprised of a subscription module 51, alarm generation logic 52, a store of or access to a store of minimum bed configuration information 53 per patient fall risk type, a store or access to a store of patient fall risk profile information 54, and a store or access to a store of current bed configuration state or information 55. Although the stores 53, 54 and 55 are illustrated in FIG. 5 as being local to the client 42, this does not have to be the case. These stores can be located in temporary storage (buffer memory) associated with the client 42 or these stores can be located in a main memory in the server, or it can be located in any memory that is accessible by the client 42 over a local or wide area network. The store(s) described herein can be implemented in any one or a combination of computer data storage technologies, such as semiconductor, magnetic or optical technologies for example. The subscription module 51 generally operates to send standard subscription request messages to one or more servers, connected to a healthcare system network, that can store information of interest to the client, such as EMR or bed configuration information. Once a response to a subscription request is received by the module 51, the event processing function 41 will automatically start to receive information currently stored in the record associated with the subscription request. This information can be for example, information regarding the current configuration state of one or more beds and this state information can be saved in a store 55 associated with or accessible by the client 42. Alternatively, the client 42 may not subscribe to receive bed configuration state information, but rather a healthcare server can periodically publish current bed configuration state information to some or all of the healthcare clients connected to the healthcare network.

Continuing to refer to FIG. 5, the minimum bed configuration store 53 is comprised of information similar to that described with reference to FIG. 3A, the patient fall risk profile store 54 is comprised of information similar to that described with reference to either FIG. 3B or 3C, and the current bed configuration state store 55 is comprised of information similar to that described with reference to FIG. 3D. Finally, the alarm generation logic 52 is comprised of a computer program that operates to determine whether or not to generate an alarm based upon information included in the stores 53, 54 and 55 (or alternative only stores 54 and 55). More specifically, in one embodiment the logic 52 can operate to examine a patient's fall risk profile, associated minimum bed configuration, and the current bed configuration state. If the current bed configuration state indicates that the patient is in their bed, the logic proceeds to determine if the current bed configuration meets the minimum bed configuration for the patient (i.e., which rails are up or down, bed heights, etc.). If the current bed configuration meets the minimum bed configuration for that patient, then the logic 52 does not generate an alert. On the other hand, if the current bed configuration does not meet the minimum bed configuration for that patient, then an alert is generated. Alternatively, the logic 52 only needs to examine the patient fall risk profile 54 if the fall risk criteria and the bed configuration profile information are stored here.

The operation of the alarm generation logic 52 will now be described with reference to the flow diagram of FIG. 6. While FIG. 6 and the following description are directed to an embodiment in which fall risk criteria and patient bed configuration information corresponding to the patients fall risk criteria are not entering into the healthcare system server, it should be understood that this information can be entered into the system and employed by the logic 52 in order to determine whether or not to generate an alert. In step 1 of the flow diagram, a hospital worker can define one or more generic patient fall risk types and enter these types into a healthcare system of storage on a server such as server 11 in FIG. 1. These fall risk types can be identified by the terms high (high fall risk), medium (medium fall risk), low (low fall risk), they can be identified in descending numerical order from a highest to lowest fall risk, or the fall risk type can be define in some other manner. Each generic fall risk type can be associated with a set of generic patient fall risk criteria. The fall risk criteria set can include, among other things, the degree to which a patient can balance while standing and the type of assistance (cane, walker, hospital worker) the patient needs in order to remain standing, it can include whether the patient has any broken limbs, and it can include physiological measures such as whether the patient has vertigo. Each fall risk type can be associated with a minimum bed configuration which is comprised of such things as whether one or more bed rails are up or down, the tilt angle of the bed and the height of the bed above the floor level. In step 2, a hospital worker can evaluate whether or not a patient is at risk or falling, and if they are the process proceeds to Step 4, otherwise the process ends at step 3. In Step 4, the hospital worker can evaluate the degree to which the patient is at risk of falling and assign them to one of the fall risk types entered into the system in Step 1. The assigned risk type can then be entered into the patients EMR. At this point, a healthcare system has information that is necessary in order to generate an alert indicating that a patient may be at risk of falling at some point in the future.

Figure 6A:
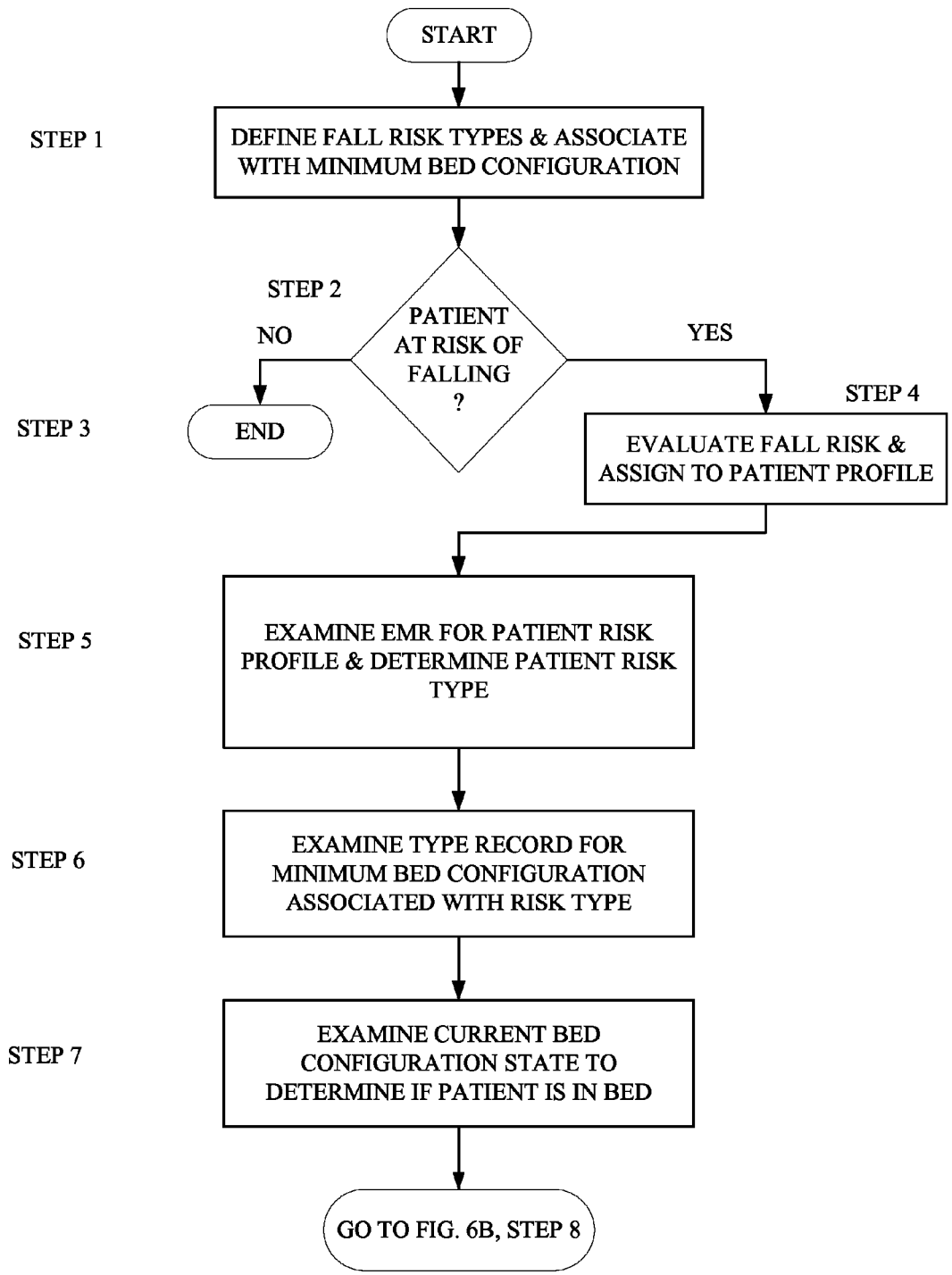
FIG. 6 is a logical flow diagram of one embodiment of the invention.
Figure 6B:
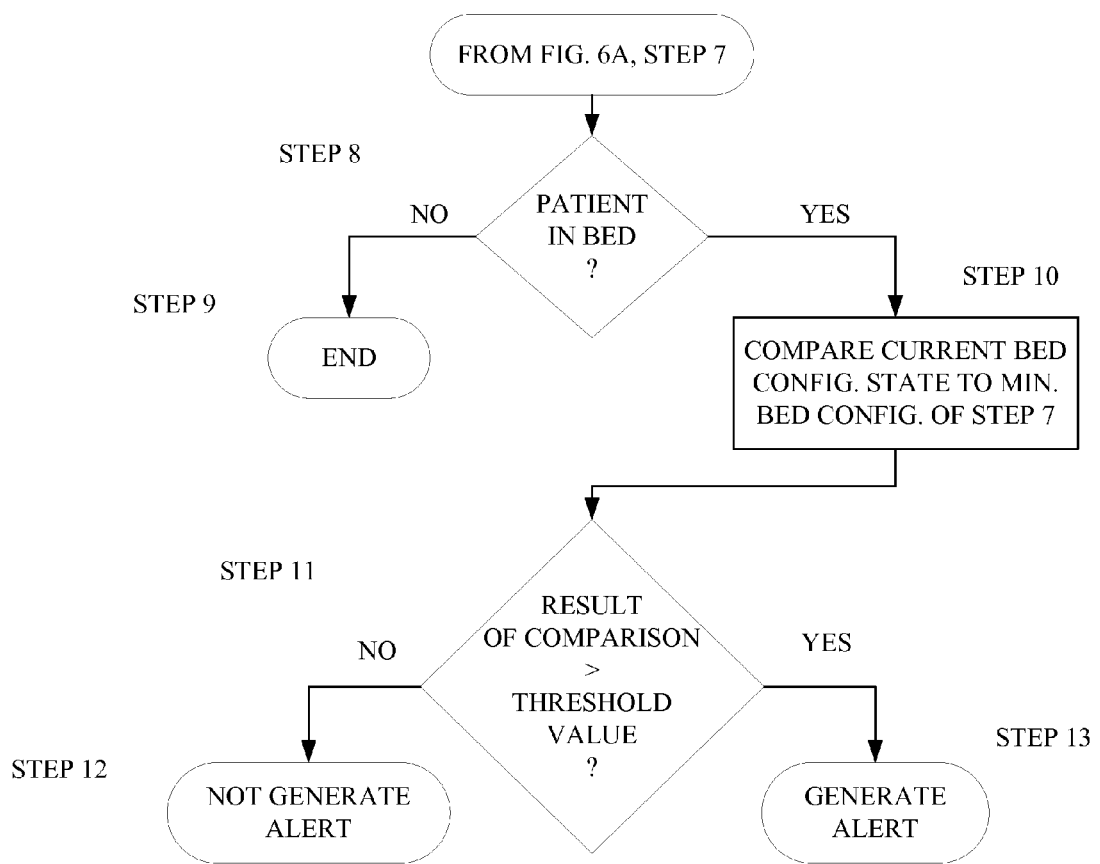

Continuing to refer to FIG. 6, in Step 5 of the process the logic 52 can examine a patient's fall risk profile stored in the patient's EMR in order to determine the patients fall risk type. Based upon the fall risk type, the logic 52 can then, in Step 6, look up minimum bed configuration information stored in the table/record described with reference to FIG. 3A. Next, in Step 7 the logic 52 can then examine the current bed configuration state described with reference to FIG. 3D, and compare this current state to the minimum bed configuration information detected as the result of Step 6. Then, in Step 8 the logic 52 can employ information detected in Step 7 to determine whether a patient is currently in their bed, and if not the process proceeds to Step 9 and no alert is generated. On the other hand, if in Step 8 the logic 52 determines that a patient is in their bed, the process proceeds to Step 10 where the state of the current bed configuration detected in Step 7 is compare to the minimum bed configuration for that patient detected in Step 6. If, in Step 11, the comparison performed in Step 10 determines that the current bed configuration does not meet the minimum bed configuration necessary to adequately protect the patient from falling out of the bed (i.e. the value of the comparison is greater than a pre-determined threshold value), the process proceeds to Step 13 and an alert is generated and sent to a call station or directly to a hospital worker. On the other hand, the process proceeds to Step 12 if the result of the comparison performed in Step 10 indicates that the current bed configuration does meet the minimum configuration necessary to prevent the patient from fall out of the bed.

The forgoing description, for purposes of explanation, uses specific nomenclature to provide a thorough understanding of the invention. However, it will be apparent to one skilled in the art that specific details are not required in order to practice the invention. Thus, the forgoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

We claim:

1. A method of alerting one or more healthcare workers to a hospital bed properties configuration which elevates a fall risk for a patient, comprising:
    linking a plurality of hospital beds over a network to a healthcare system:
        wherein the hospital beds comprise one or more sensors to monitor one or more hospital bed properties, the sensors operative to detect a state of each hospital bed property and to generate a signal indicative of the state of each hospital bed property for transmission over the network to the healthcare system; and
        wherein the healthcare system comprises one or more servers each of which have non-transitory computer storage for maintaining at least one patient electronic medical record, for maintaining information relating to a current hospital bed properties configuration received from at least one hospital bed, and for storing computer program logic to assess a patients risk of falling;
    creating a fall risk profile for the patient, and using information in the patient's fall risk profile to determine a minimum hospital bed properties configuration necessary to mitigate the patient's risk of falling;
    storing information associated with the patient's minimum hospital bed properties configuration in the at least one patient electronic medical record maintained by the healthcare system;
    configuring properties of a hospital bed assigned to the patient to comply with the minimum hospital bed properties configuration information stored in the patient's electronic medical record;
    detecting a current state of the properties associated with the patient hospital bed and sending information indicative of the detected property states over the network to the healthcare system; and
    the healthcare system generating and sending an alert over the network to one or more hospital workers indicating an elevated patient fall risk if the computer program logic determines that current hospital bed property configuration status information indicates that the patient is present in the hospital bed and the information does not meet the minimum hospital bed properties configuration necessary to mitigate the patient fall risk.

2. The method of claim 1, further comprising the healthcare worker modifying the current hospital bed property configuration to meet the minimum hospital bed properties configuration and the healthcare system detected the modification to the current hospital bed properties.

3. The method of claim 2, further comprising the healthcare system cancelling the alert sent to the one or more hospital workers or sending a second alert to the one or more healthcare workers indicating that the patient is no longer at risk of falling.

4. The method of claim 1, wherein the one or more hospital bed properties is comprised of one or more bed rail type identities, bed height sensing, bed tilt sensing, and patient weight and position sensing.

5. The method of claim 1, wherein the one or more hospital bed property states comprise any one or more of the location of the hospital bed, the position of one or more bed rails, the elevation of the bed surface with respect to a surface upon which the bed rests, and whether a patient is currently in the bed, their weight and position on the bed surface.

6. The method of claim 1, wherein the electronic medical record comprises any one or more of the identity of the patient, the identity of the hospital bed assigned to the patient, the location of the hospital bed, and patient fall risk profile.

7. The method of claim 1, wherein the computer program logic operates on information comprising the minimum hospital bed properties configuration, the patient fall risk profile and the current state of the patient hospital bed properties.

8. The method of claim 1, wherein the patient fall risk profile is comprised of the patient identity and a generic fall risk type or the patient identity, one or more patient fall risk criteria and a minimum bed properties configuration.

9. The method of claim 8, wherein the one or more patient fall risk criteria is comprised a description of symptoms affecting the patients mobility or ambulatory characteristics.

10. The method of claim 9, wherein the symptoms comprise one or both of a physical and physiological characteristic.

11. The method of claim 10, wherein the minimum hospital bed properties configuration comprises a listing of the state of one or more bed properties that are necessary to mitigate the patient fall risk.

12. The method of claim 1, wherein the current state of the patient hospital bed properties changes every time at least one hospital bed property changes.

13. A method of alerting one or more healthcare workers to a hospital bed properties configuration which elevates a fall risk for a patient, comprising:
    linking a plurality of hospital beds over a network to a healthcare system:
        wherein the hospital beds comprise one or more sensors to monitor one or more hospital bed properties, the sensors operative to detect the state of each hospital bed property and to generate a signal indicative of the state of each hospital bed property for transmission over the network to the healthcare system; and
        wherein the healthcare system comprises one or more servers each of which have non-transitory computer storage for maintaining at least one patient electronic medical record and for maintaining information relating to a current hospital bed properties configuration received from at least one hospital bed, each of the one or more servers being programmed to assess a patients risk of falling;

defining a plurality of generic fall risk types each of which type is indicative of the degree to which a patient is at risk of falling;

assigning a set of bed property states to each generic fall risk type, the set of bed property states representing a minimum bed properties configuration necessary to mitigate the patients risk of falling;

creating a fall risk profile for the patient, and assigning, based upon information comprising the patient's fall risk profile, an appropriate one of the plurality of the generic fall risk types to the patient and entering the patients generic fall risk type into the patient's electronic medical record maintained by the healthcare system;

assigning the patient to one of the plurality of the hospital beds and configuring the state of each hospital bed property to be the same as the property states associated with the patient's generic fall risk type stored in their electronic medical record;

detecting a current state of the properties associated with the patient's hospital bed and sending information indicative of the detected property states to the healthcare system; and the healthcare system generating and sending to one or more hospital workers an alert indicating an elevated patient fall risk if the current hospital bed property configuration state information indicates that the patient is present in the hospital bed and the information does not meet the minimum hospital bed properties configuration necessary to mitigate the patient fall risk.

14. The method of claim 13, further comprising the healthcare worker modifying the current hospital bed property configuration to meet the minimum hospital bed properties configuration and the healthcare system detected the modification to the current hospital bed properties.

15. The method of claim 14, further comprising the healthcare system cancelling the alert sent to the one or more hospital workers or sending a second alert to the one or more healthcare workers indicating that the patient is no longer at risk of falling.

16. The method of claim 14, wherein the patient fall risk profile is comprised of the patient identity and a generic fall risk type or the patient identity, one or more patient fall risk criteria and a minimum bed properties configuration.

17. The method of claim 16, wherein the generic fall risk type is comprised of any one or a high fall risk, a medium fall risk and a low fall risk.

18. The method of claim 13, wherein the one or more hospital bed properties is comprised of one or more bed rail type identities, bed height sensing, bed tilt sensing, and patient weight and position sensing.

19. The method of claim 13, wherein the one or more hospital bed property states comprise any one or more of the location of the hospital bed, the position of one or more bed rails, the elevation of the bed surface with respect to a surface upon which the bed rests, and whether a patient is currently in the bed, their weight and position on the bed surface.

20. The method of claim 13, wherein the electronic medical record comprises any one or more of the identity of the patient, the identity of the hospital bed assigned to the patient, the location of the hospital bed, and patient fall risk profile.

21. The method of claim 13, wherein the computer program logic operates on information comprising the minimum hospital bed properties configuration, the patient fall risk profile and the current state of the patient hospital bed properties.

22. The method of claim 13, wherein the minimum hospital bed properties configuration comprises a listing of the state of one or more bed properties that are necessary to mitigate the patient fall risk.

23. The method of claim 13, wherein the current state of the patient hospital bed properties changes every time at least one hospital bed property changes.

24. A system for alerting one or more healthcare workers to a hospital bed properties configuration which elevates a fall risk for a patient, comprising:

a plurality of hospital beds linked over a network to a healthcare system:

wherein at least one of the plurality of hospital beds is configured to monitor the state of one or more hospital bed properties and to transmit information indicative of the properties over the network to the healthcare system; and wherein the healthcare system comprises one or more servers each having non-transitory computer storage for maintaining patient information, current hospital bed properties configuration information, and for storing program logic used to assess the patient fall risk and to send an alert to one or more healthcare workers indicating an elevated patient fall risk if the current hospital bed property configuration state information indicates that the patient is present in the hospital bed and the current hospital bed property configuration state information does not meet a minimum hospital bed properties configuration that is determined by a patient fall risk profile and which is stored in an electronic medical record associated with the patient.

* * * * *